(12) United States Patent
Hermiz

(10) Patent No.: US 8,491,849 B2
(45) Date of Patent: Jul. 23, 2013

(54) WRITING IMPLEMENT SANITIZER AND METHOD OF SANITIZATION THEREFOR

(76) Inventor: Raad Hermiz, Las Vegas, NV (US)

( * ) Notice: Subject to any disclaimer, the term of this patent is extended or adjusted under 35 U.S.C. 154(b) by 0 days.

(21) Appl. No.: 13/158,243

(22) Filed: Jun. 10, 2011

(65) Prior Publication Data

US 2012/0315187 A1     Dec. 13, 2012

(51) Int. Cl.
*A61L 2/18*     (2006.01)

(52) U.S. Cl.
USPC ......................................................... 422/292

(58) Field of Classification Search
USPC .................................................. 422/292, 28
See application file for complete search history.

(56) References Cited

U.S. PATENT DOCUMENTS

| | | | | | |
|---|---|---|---|---|---|
| 4,474,195 A | * | 10/1984 | Warner | ........................... | 132/73 |
| 4,964,372 A | * | 10/1990 | Zeenni et al. | ................ | 132/74.5 |
| 5,065,778 A | * | 11/1991 | Terrell | ......................... | 132/74.5 |

* cited by examiner

*Primary Examiner* — Sean E Conley
(74) *Attorney, Agent, or Firm* — Weide & Miller, Ltd.

(57) ABSTRACT

A writing implement sanitizer rapidly cleans and sanitizes writing implements for public or personal use. The writing implement sanitizer may comprise a sanitization container having sanitizer fluid or material therein. A membrane may be positioned within the sanitization container and may have one or more resilient or elastic openings configured to accept one or more writing implements. A cover may be used to enclose the sanitization container. In operation, a user may insert a writing implement into and through an opening in the membrane and into the sanitizer fluid. This action cleanses and sanitizes the writing implement. Further cleansing may then be provided and sanitizer fluid may be removed by a removal action whereby the writing implement is removed from the membrane.

13 Claims, 3 Drawing Sheets

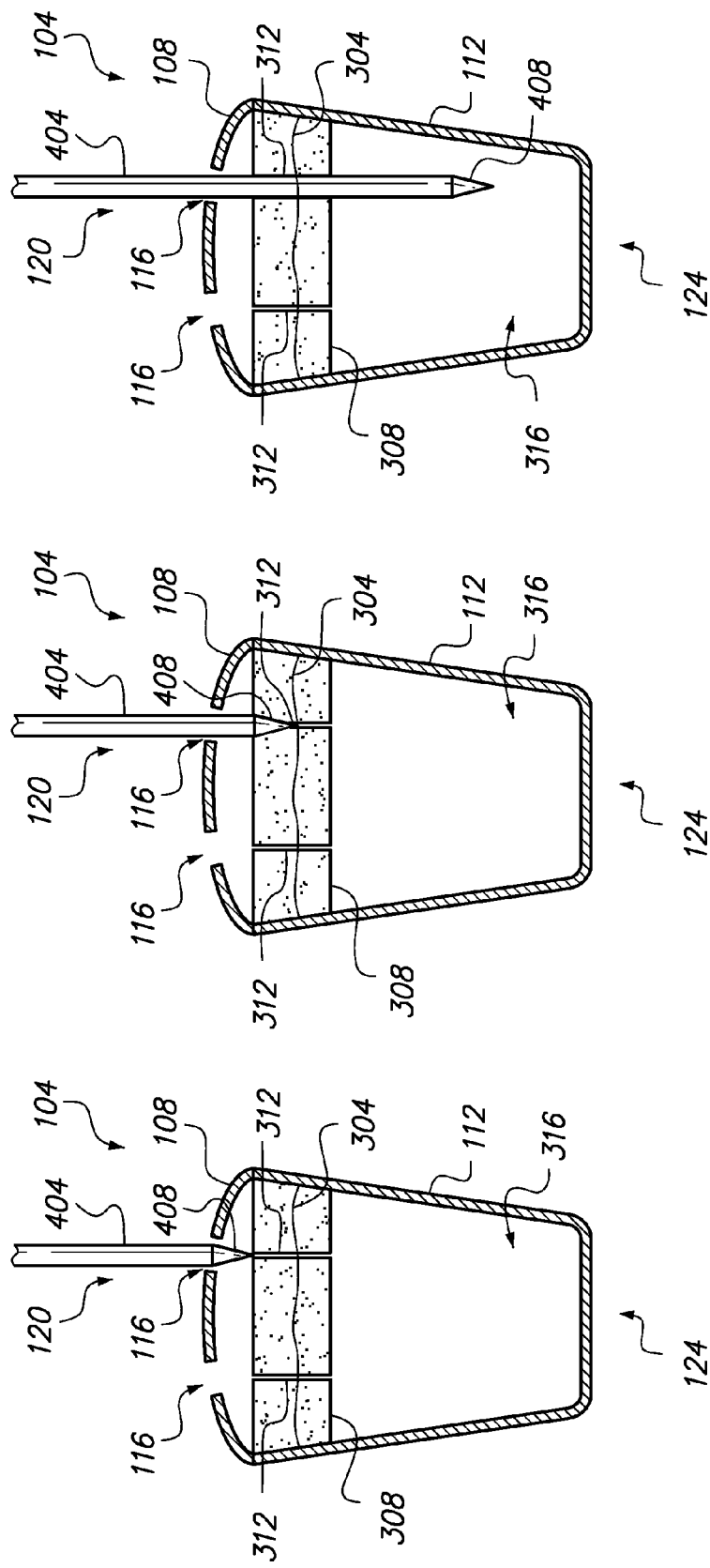

WRITING IMPLEMENT SANITIZER AND METHOD OF SANITIZATION THEREFOR

BACKGROUND OF THE INVENTION

1. Field of the Invention

The invention relates generally to sanitization or cleaning apparatus, and in particular to a writing implement sanitizer and method of sanitization.

2. Related Art

Germs causing mild to serious sickness can live on a variety of surfaces for long periods of time. The spread of germs is facilitated by close proximity or contact between individuals and other people or items carrying such germs. Cleaning or washing has generally been used to clean various surfaces. In public spaces this is mostly done for aesthetic purposes, and it may be at least unclear how "clean" a surface truly is. For example, at a restaurant tables and chairs are often wiped, giving such surfaces a clean appearance. However, it is generally unknown how "clean" the tables and chairs truly are. For instance, a clean table may actually bear a number of harmful germs.

This is undesirable especially when considering that germs thrive on increased contact with more individuals. Sickness can spread rapidly from one person to many as additional people are exposed to or contact sickness spreading germs. The more individuals that come into contact with the germs the more likely that the germs will contact someone susceptible to their harmful effects.

In addition, there are public areas that are configured to provide a sanitary environment and public areas where such environment is more difficult to provide. For instance, it is known that a public bathroom may be an environment where harmful germs are likely to exist and thus soap and hand washing facilities are provided. At other public areas, it may be difficult to provide a sanitary environment due to their configuration.

From the discussion that follows, it will become apparent that the present invention addresses the deficiencies associated with the prior art while providing numerous additional advantages and benefits not contemplated or possible with prior art constructions.

SUMMARY OF THE INVENTION

A writing implement sanitizer and method of sanitization is disclosed herein. The writing implement sanitizer allows users to quickly and easily cleanse and/or sanitize one or more writing implements. This allows a clean and sanitary environment to be provided. The writing implement sanitizer removes dirt, debris, and other unwanted material from a writing implement. In addition, the writing implement sanitizer can remove germs and bacteria from the writing implement. In this manner, the spread of dirt, debris and germs or bacteria via a writing implement is greatly reduced, if not eliminated.

The writing implement sanitizer may have various configurations. For example, in one exemplary embodiment a writing implement sanitizer may comprise a sanitization container having an open portion and forming a watertight compartment configured to hold one or more sanitizer fluids therein. A membrane comprising a resilient material may extend between one or more walls of the sanitization container. One or more openings configured to accept at least one writing implement may extend through the membrane. A cover may be above the membrane and configured to at least partially enclosing the open portion of the sanitization container. The cover may comprise one or more openings configured to align with the openings of the membrane. The cover may be releasably attached to the sanitization container. It is noted that the openings of the cover are larger than the openings of the membrane.

The membrane may be held in position in various ways. For example, the membrane may be attached to at least one wall of the sanitization container. In addition or alternatively, a shelf configured to support the membrane may be formed in at least one wall of the sanitization container. It is contemplated that the membrane may be secured to the cover as well.

In another exemplary embodiment, the writing implement sanitizer may comprise a sanitization container configured to hold one or more sanitizers having an open top, and a cover over the open top of the sanitization container. The cover may have one or more openings configured to accept at least one writing implement therein. It is noted that the sanitizers are one or more liquid sanitizers.

A membrane having one or more openings aligned with the openings of the cover may be below the cover. The membrane may comprise one or more resilient materials at the openings. This allows the openings to accommodate a writing implement. The membrane may have a planar shape, a thicker block like shape, or other shapes. The membrane may be formed from a resilient material selected from the group consisting of sponge, foam, and rubber, and silicone.

The openings of the membrane will typically be configured to accept at least one writing implement therein. The openings of the cover may be larger than the writing implement, and the openings of the membrane may be smaller than the implement.

Various methods of sanitizing a writing implement are disclosed herein as well. For example, a method of sanitizing a writing implement with a writing implement sanitizer may comprise providing a sanitization container for holding one or more sanitizers therein, providing a cover to cover an open portion of the sanitization container, and forming one or more openings in the cover to accept at least one writing implement. A membrane comprising resilient material secured may be provided below the cover. Typically, one or more openings that are smaller than a diameter of the writing implement will be formed in the membrane.

The openings of the membrane may be aligned with the openings of the cover to allow a writing implement to be accepted into both an opening of the cover and an opening of the membrane. For example, a writing implement may be accepted by receiving the writing implement in the openings of the cover and the openings of the membrane.

One or more sanitizers may be received in the sanitization compartment. An exterior surface of a writing implement may then be cleansed through contact between the writing implement and at least one opening of the openings in the membrane as the writing implement is moved within the opening.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

FIG. 4A is a cross sectional side view of an exemplary pen sanitizer in a first state of use;

FIG. 4B is a cross sectional side view of an exemplary pen sanitizer in a second state of use; and FIG. 4C is a cross sectional side view of an exemplary pen sanitizer in a third state of use.

DETAILED DESCRIPTION OF THE PREFERRED EMBODIMENTS

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

In general, the pen sanitizer provides an apparatus by which pens, pencils, and/or other writing implements may be quickly and easily sanitized. Typically, the writing implement sanitizer will be self contained and thus does not require external supporting equipment in order to function. For example, unlike washing machines or washing stations, the pen sanitizer does not require external plumbing hookups, electrical connections, or other external support/resources. In this manner, the writing implement sanitizer is self contained, portable, and convenient.

As will be disclosed below, the writing implement sanitizer allows writing implements to be quickly and easily sanitized, without hindering their ability to write or otherwise damaging the implements. It is noted that though described with regard to a writing implement herein, the writing implement sanitizer may be configured to sanitize a variety of items having a similar configuration.

Figure 1:
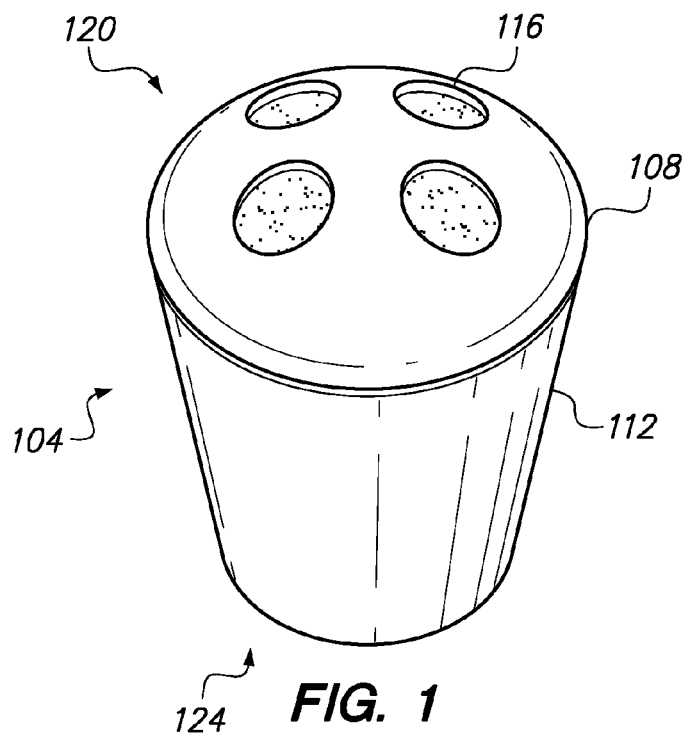
FIG. 1 is a perspective view of an exemplary pen sanitizer.
Figure 2:
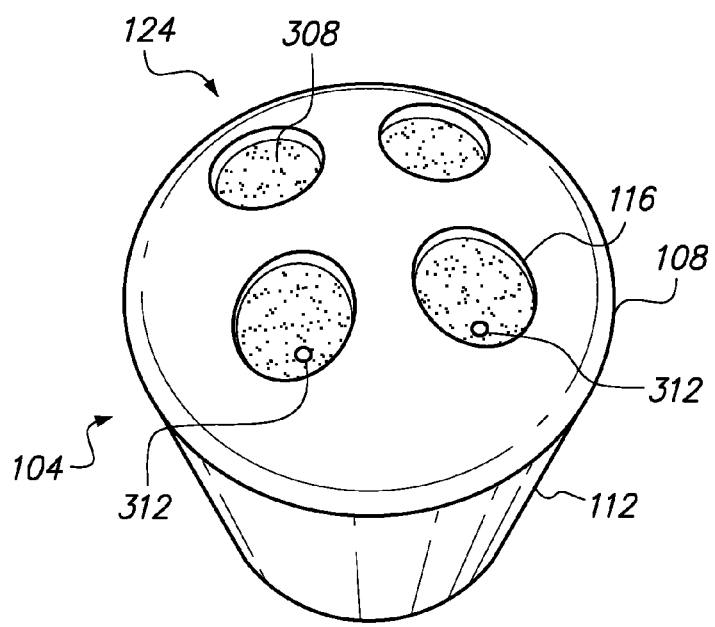
FIG. 2 is a top perspective view of an exemplary pen sanitizer.

The writing implement sanitizer will now be described with regard to FIGS. 1-2. FIG. 1 is a perspective view showing the side and top of the writing implement sanitizer 104, while FIG. 2 is a top perspective view showing more of the top of the writing implement sanitizer. In one or more embodiments, the writing implement sanitizer 104 may have a top end 120 and a bottom end 124. A cover 108 may be at the top end 120 and cover or enclose (at least partially) a sanitization container 112. As will be described further below, the cover 108 may be used to cover an open end or open portion of the sanitization container 112. This helps protect an interior compartment of the sanitization container 112, preventing containments from entering the interior compartment where writing implement sanitation occurs. In addition, this helps reduce evaporation of sanitation fluid held within the sanitization container, if provided.

The cover 108 may have one or more openings 116, such as shown in FIG. 1. These openings 116 are generally configured to accept one or more writing implements. Typically, an opening 116 will be configured to accept a single writing implement. For example, as shown, the openings 116 in the cover 108 of FIGS. 1-2 are sized to accept the diameter of a writing implement. The openings 116 also allow the cover 108 at least partially (and sometimes substantially) cover the open end of the sanitization container 112, while allowing writing implements to enter the sanitization container.

The openings 116 provide the additional benefit of guiding writing implements as they are sanitized using the writing implement sanitizer 104. For instance, the openings 116 locate a writing implement at a particular position for sanitization. This is because a user would be unable to insert a writing implement into the sanitization container 112 unless the writing implement is properly located at an opening 116. As will be described further below, the proper positioning of the writing implement helps ensure that sanitization of the writing implement is effective.

Various numbers of openings 116 may be provided. The embodiments illustrated have four openings 116 for example. In one embodiment, only a single opening 116 may be provided. It is contemplated that the size of the writing implement sanitizer 104 can be reduced where fewer openings 116 are provided. For example, a writing implement sanitizer 104 having a single opening 116 may be a narrower cylindrical or other shape than one having multiple openings.

The openings 116 may have various shapes and sizes. For example, the openings may be circular, square, polygonal, or various other shapes. In one embodiment, the openings 116 may correspond in shape to a cross sectional shape for one or more writing implements. For example, polygonal openings 116 may be provided for mechanical or wooden pencils having a polygonal cross sectional shape. Round openings 116 may be provided for pens having a round cross section shape. It is contemplated that the size of the openings 116 may be adjusted to accept writing implements of various diameters. The openings 116 may be enlarged at least somewhat to allow writing implements of various diameters to be accepted therein.

It is also contemplated that the openings 116 may be sized for one or more particular writing implements. For example, in one embodiment, the openings 116 may match the diameter (and/or peripheral shape) of a particular writing implement. In this manner, the openings 116 ensure only particular writing implements can be used with the writing implement sanitizer 104. This may be beneficial in public areas where a business or other entity only wishes for its writing implements to be sanitized. In addition, an opening 116 having a matching size can help precisely guide a writing implement into the writing implement sanitizer 104.

In embodiments with multiple openings 116, one or more of the openings 116 may have different shapes and/or sizes. This is advantageous in that writing implements of various sizes may be used. In addition, a user may select the opening 116 with the closest size and/or shape to his or her writing implement. In this manner, the opening 116 can better guide the writing implement into and out of the writing implement sanitizer 104 during use.

As will be described further below, the sanitization container 112 will typically be used to contain elements of the writing implement sanitizer 104 used to sanitize writing implements. This is why the sanitization container 112 may be configured as a container.

The sanitization container 112 may have various shapes and sizes. In general, the shape of the sanitization container 112 at its opening will typically match that of the cover 108 (or a portion thereof), or vice versa, so that the cover can enclose the opening of the sanitization container.

In general, the sanitization container 112 will be of a height sufficient to hold the sanitization elements therein while allowing a sufficient portion of a writing implement to be inserted therein. For example, the bottom third, half, or three quarters of a writing implement could be inserted into the writing implement sanitizer 104 in one or more embodiments. In one or more embodiments, the extent to which a writing implement is inserted governs the amount of the writing implement that will be sanitized. Typically, users most commonly contact writing implements near their tip. This area also encounters the most contact time with users. Thus, it is contemplated that a writing implement sanitizer 104 may be configured to accept at least a portion of the bottom end (near the writing tip) of a writing implement. For instance, as stated, the writing implement sanitizer 104 could be configured to accept the bottom third or half of a writing implement. It is contemplated that less or more of a writing implement could be accepted in various embodiments of the writing implement sanitizer 104.

As shown in FIGS. 1-2, the writing implement sanitizer 104 has a rounded shape. It is contemplated that the writing implement sanitizer 104 may be various shapes (and sizes). For example, the writing implement sanitizer 104 may be rounded (such as shown), square, rectangonal, and various other shapes. The writing implement sanitizer 104 could also be various sculpted shapes and/or shapes that resemble people, animals, objects, or portions thereof.

Figure 3A:
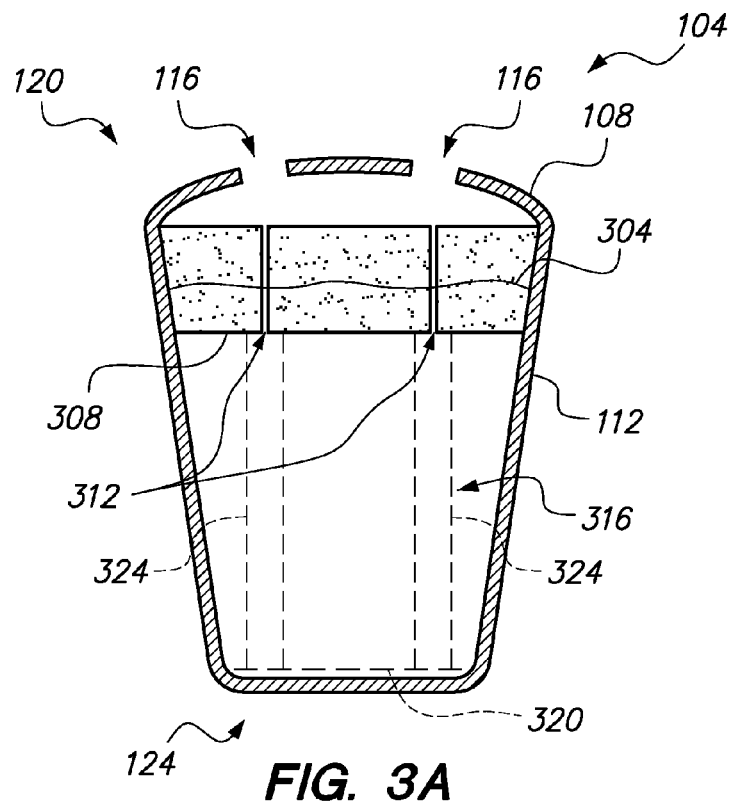
FIG. 3A is a cross sectional side view of an exemplary pen sanitizer.

FIG. 3A provides a side cross sectional view of the writing implement sanitizer 104. As can be seen, the cover 108 is at a top end 120 of the writing implement sanitizer 104 and enclosing an open end of the sanitization container 112. As can also be seen, the cover 108 may be configured to fit over or on top of the sanitization container 112 to cover the sanitization container. It is contemplated that the cover 108 may be integrally formed to the sanitization container 112, or may be removable in one or more embodiments. Typically the cover 108 will be removable so as to allow access to an internal portion of the writing implement sanitizer 104, such as for part replacement, maintenance, sanitation fluid refills/replacement, and/or cleaning.

In one or more embodiments, the writing implement sanitizer 104 may comprise a resilient membrane 308 used to sanitize a writing implement. The resilient membrane 308 may have one or more openings 312 therein. In general, these openings 312 accept the shaft or member of a writing implement during use of the writing implement sanitizer 104. As can be seen for example, the membrane 308 has openings 312 corresponding to the openings 116 in the cover 108. In this manner, a writing implement may be inserted through the cover 108 and into the openings 312 of the membrane 308, as will be described further below.

It is contemplated that the membrane 308 may form a layer within the writing implement sanitizer 104. For instance, as shown, the membrane 308 extends laterally between the sides of the sanitization container 112. In this manner, the membrane 308 can be attached to the sides of the sanitization container 112 to hold the membrane in position while ensuring the openings 312 of the membrane are aligned relative to the openings 112 of the cover 108. In some embodiments, the membrane 308 may be held by a friction fit to the sanitization container 112. In other embodiments, one or more fasteners or support structures may hold the membrane 308 in position.

For example, the membrane's peripheral edge and the sanitization container's internal edge may have one or more threads or the like. In this manner, the membrane 308 may be rotated in a first direction to secure the membrane, and be rotated in another direction to remove the membrane. As another example, the membrane 308 may be held in place by a snap fit using one or more outwardly extending tabs that engage inward depressions or detents respectively in the membrane and the sanitization container 112, or vice versa. The sanitization container 112 could also or alternatively have a shelf formed at its top. For example, the walls or sides of the sanitization container 112 may be thinner at the top to form a lip or shelf (inside the sanitization container) that supports the membrane 308. One or more mechanical fasteners, such as pins or screws could be used to hold the membrane 308 in position as well. It is contemplated that hook and loop fasteners could form mating or contact surfaces on the membrane 308 and sanitization container 112 to fasten the membrane in position. One or more adhesives may be used as well. It is noted that the membrane 308 may be held in position in various other ways so long as the membrane is kept in position when a writing implement is inserted and/or removed.

Figure 3B:
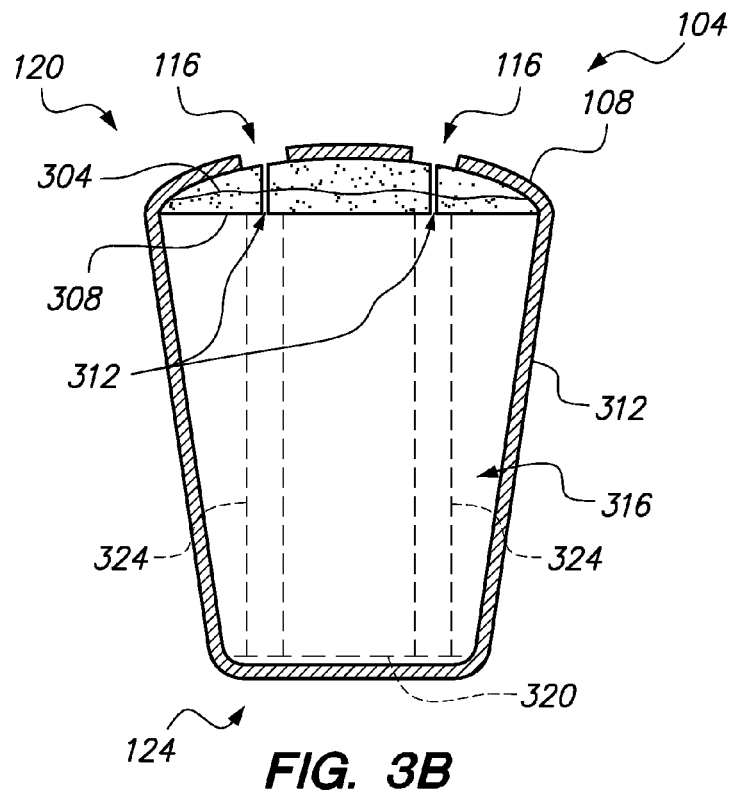
FIG. 3B is a cross sectional side view of another exemplary pen sanitizer.

In some embodiments, the membrane 308 may be secured to the cover 108 rather than or in addition to the sanitization container 112. For example, the membrane 308 may be attached to a surface or other structure of the cover 108, such as shown in FIG. 3B. In this manner, the membrane 308 may be removed with the cover 108, such as for replacement, cleaning, or other operations. It is contemplated that multiple membranes 308 may be provided. For instance, a first membrane 308 may be at the cover 108 while a second membrane is at the sanitization container 112. This configuration may be used to provide a two-stage sanitization process. In such cases, the membranes may be different materials or configurations. For example, one membrane may be less elastic than another at its openings 312. It is contemplated that multiple membranes 308 could be secured to a sanitization container 312, cover 308, or both.

The membrane 308 or one or more portions thereof may be formed from resilient material. For example, the openings 312 may be formed in resilient portions of the membrane 308. This permits the openings 312 to expand to accept a writing implement, and contract around the writing implement to assist with its sanitization. It is noted that the entire membrane 308 may be a resilient material in some embodiments. In other embodiments, the membrane 308 may comprise a rigid or semi-rigid support structure which holds resilient material in which the openings 312 may be formed. For example, the membrane 308 may be a plastic structure having rubber or foam openings 312. Some other exemplary resilient materials that could be used include, sponge, silicone, and other elastic materials. In some embodiments, materials may be selected because they are capable of absorbing and distributing sanitation fluid or the like to a writing implement. For example, sponge or foam may be used since such material may "soak up" sanitation fluid and apply it to a writing implement at the openings 312 of the membrane 308.

The membrane 308 may have various thicknesses. For example, as shown in FIG. 3A the membrane 308 has a relatively thick configuration, but does not extend to the bottom of the sanitization container 112. As can be seen, the openings 312 extend vertically through the membrane 308 some distance due to this thickness. The increased thickness is beneficial in that it increases the surface contact area between the openings 312 and a writing implement. It is contemplated that the membrane 308 could extend to the bottom of the sanitization container 112 in some embodiments though this may increase resistance to writing implements being inserted and removed from the membrane.

Membranes 308 may be thinner in some embodiments. For example, a membrane 308 may be a planar structure in some embodiments. To illustrate, a rubber sheet or sheet of other resilient material may form a membrane 308 or portion thereof in some embodiments. Such membranes 308 may be constructed as described above.

It can be seen from FIGS. 3A-3B that the sanitization container 112 is capable of holding sanitizer fluid 304 therein. In one or more embodiments, the amount of sanitizer fluid 304 may be set such that it contacts some or all of the membrane 308. In this manner, the membrane 308 can soak up the sanitizer fluid 304 and transfer it to a writing implement. It is contemplated that the writing implement sanitizer 104 could have a fluid level sensor and alarm. In this manner, when the sanitizer fluid 304 is low (e.g., below the level of the membrane 308) and alarm or indicator (e.g., speaker or light) may be triggered informing a user to refill the sanitizer fluid.

It is noted that sanitizer fluid 304 need not be used in all embodiments. For example, it is contemplated that a sanitizer fluid 304 may be various sanitizers, such as in the form of a gel (or various other viscosities) in some embodiments. Sanitizers (including sanitizer fluid) may include agents which remove dirt, debris, and the like and/or kill germs and bacteria or inhibit growth of the same.

The sanitizer fluid 304 may have cleansing and/or sanitizing qualities. For example, the sanitizer fluid 304 may comprise one or more soaps or similar cleansers. In addition or alternatively, the sanitizer fluid 304 may have disinfectant or antimicrobial properties to eliminate microbes or bacteria. In general, the sanitizer fluid 304 operates in cooperation with the membrane 308 to sanitize a writing implement. For example, the sanitizer fluid 304 may have a degreaser component which is applied to a writing implement via the membrane 308. It can be seen that the writing implement sanitizer 104 can clean and disinfect a writing implement in this manner.

The sanitization container 112 may have one or more additional components which are also shown in FIGS. 3A-3B. For example, the sanitization container 112 may have a pad 320 at its bottom to cushion the tip of a writing implement if such tip should reach the bottom of the sanitization container. This helps prevent damage to the tip since the sanitization container may be a rigid material. In addition, this provides feedback to the user that he or she has hit the bottom of the sanitization container 112. It is noted that the pad 320 need not be provided in all embodiments.

The sanitization container 112 may also include one or more writing instrument guides 324. Such guides 324 may be aligned with the openings 312 of the membrane 308. The guides 324 may be channels below the membrane 308 which guide the direction of a writing implement as it is inserted beyond the membrane 308. This helps keep the writing implement aligned during sanitization. This also prevents a writing implement from being moved side to side and potentially stretching out the openings 312 of the membrane 308. The guides 324 may extend upward from the bottom of the sanitization container 112 in one or more embodiments. In addition or alternatively, the guides 324 may be held in position by one or more lateral braces extending from a side or wall of the sanitization container 112. It is noted that the guides 324 are optional and need not be included in all embodiments.

Operation of the writing implement sanitizer 104 will now be described with regard to FIGS. 4A-4C. As can be seen, the writing implement sanitizer 104 is used to cleanse and sanitize a writing implement 404 in the form of a pen in FIGS. 4A-4C. As disclosed above, various other writing implements may be cleansed and sanitized in the same fashion. The writing implement 404 may have a tip 408 which is typically the writing end of the writing implement. Though shown as being inserted tip 408 first, it is noted that the writing implement 404 could be inserted with its back (i.e., non-tip end) first. This is beneficial in that it allows both ends of a writing implement 404 to be sanitized.

As can be seen from FIG. 4A, the writing implement 404 may be inserted into an opening 116 of the cover 108. As discussed above, the openings 116 of the cover 108 help the user align the writing implement 404 for cleansing by indicating where a writing implement should be inserted. Once at the proper position the writing implement 404 may be inserted into an opening 312 the membrane 308, as can be seen in FIG. 4A. FIG. 4A also shows that the sanitizer fluid 304 is in contact with the membrane 308.

Referring to FIG. 4B, it can be seen that the resilient material of the membrane 308 allows the opening 312 to expand around the writing implement 404 as it is inserted. The resilient material also causes the opening 312 to collapse around the writing implement. This provides surface contact between the exterior surface of the writing implement 404 and the membrane 308 so that sanitizer fluid 304 is applied to the writing implement. In addition, the physical surface contact between the membrane 308 and writing implement 404 helps dislodge dirt, debris, and other unwanted materials from the surface of the writing implement.

FIG. 4C shows that the writing implement may be inserted beyond the membrane 308 and further into the sanitization container 112. This allows the writing implement 404 to come into direct contact with the sanitizer fluid 304 which provides additional cleansing and sanitization via one or more active compounds in the sanitizer fluid 304. Meanwhile, inserting additional sections of the writing implement 404 through an opening 312 of the membrane 308 continues to sanitize and cleanse additional sections of the writing implement. As can be seen from FIG. 4C, a substantial portion of the writing implement 404 may pass through the membrane 308 and into the sanitizer fluid 304 for sanitization at the writing implement sanitizer 104.

The writing implement 404 may be left within the sanitization container 112 for a period of time or may be immediately withdrawn. In some embodiments, the sanitizer fluid 304 may provide better cleansing and/or sanitization if the period of exposure is increased.

The writing implement 404 encounters a second pass of sanitization as it is removed from the writing implement sanitizer 104. For instance, as the writing implement 404 is withdrawn, the membrane's openings 312 continue to be in close contact with the writing implement. In this manner, additional dirt and debris may be dislodged as the writing implement 404 is removed. Moreover, the membrane 308 can function as a squeegee to thereby remove sanitizer fluid 304 from the writing implement 404. In this manner, the sanitizer fluid 304 can be retained within the sanitization container 112 by removing it from the writing implement 404 as the writing implement is removed. The removal of the sanitizer fluid from the writing implement 404 also allows the writing implement to be drier to the touch after sanitization. It is contemplated that an additional membrane for drying or removing sanitizer fluid 304 may be provided in some embodiments. For example, a sponge, cloth, foam, or similar membrane may be positioned above the first membrane to remove additional sanitizer fluid 304 as a writing implement is removed. The sanitizer fluid 304 may also be configured to rapidly evaporate. In case mechanical pencils or pens are used, a sanitizer fluid 304 may be selected for its non-corrosive qualities. Once removed from the writing implement sanitizer 104 the writing implement is sanitized and ready for use by one or more additional users.

The writing implement sanitizer 104 is easily maintained. For example, the cover 108 may be removed to refill or replace the sanitizer fluid 304. It is contemplated that the sanitization container 112 could have a releasable stopper at its bottom end. When released or opened the stopper would allow sanitizer fluid 304 to flow out of the sanitization container 112. This provides a convenient way to evacuate the sanitizer fluid 304. In addition, one or more membranes 308 could be cleaned or replaced with the cover 108 removed. For example, a membrane 308 could be detached from the sanitization container 112 and/or cover 108 for cleaning or replacement. The same cleaned membrane 308 or a new membrane may then be reattached to the sanitization container 112 and/or cover 108.

As can be seen, the writing implement sanitizer 104 provides for rapid cleansing and/or sanitization of writing implements. A merchant, store owner, or the like may thus rapidly clean writing implements for their customers, patrons, or the like. This provides a professional environment and increases customer appreciation of the provider. It is contemplated that the writing implement sanitizer 104 may be stationed near areas where writing occurs so that it may be used by customer or patrons themselves. For instance, at a bank one or more writing implement sanitizer 104 may be positioned at the teller window, or deposit/withdrawal slip preparation area for user by bank customers (and employees).

Since the writing implement sanitizer 104 provides sanitization for writing implements conveniently and quickly, it encourages the sanitization of writing implements. This is highly beneficial in that it helps prevent the spread of infectious germs. In addition, the writing implement sanitizer 104 can remove dirt, debris, and grease from writing implements. This is beneficial in that users may notice and appreciate the quality and cleanliness of the writing implements.

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

What is claimed is:

1. A writing implement sanitizer comprising:
    a sanitization container comprising:
        a body having a bottom end and a top end; and
        a cover located at said top end of said body, said cover having at least one opening therein;
        said container defining an interior area between at least said cover and said bottom end of said body;
    a sanitization membrane comprising a resilient material having a sanitizer associated therewith, said membrane located within said interior area of said sanitization container below said cover and spaced upwardly from said bottom end of said body, said membrane having one or more passages there through aligned with one or more of said openings in said cover; and
    a writing implement guide extending from a bottom of said membrane at one of said passages there through to said bottom end of said container, said guide defining a interior passage through which a writing implement may pass;
    whereby a user may pass an end of a writing implement through one of said openings in said cover and through an aligned passage through said membrane and beyond said membrane into said writing implement guide, whereby a length of said writing implement from said tip contacts said membrane for sanitization as said writing implement is moved through said membrane.

2. The writing implement sanitizer in accordance with claim 1 wherein said at least one opening in said cover is larger than the one or more passages in said membrane.

3. The writing implement sanitizer in accordance with claim 1 wherein said body has at least one wall extending upwardly between said bottom end and said top end and said membrane is attached to said at least one wall.

4. The writing implement sanitizer in accordance with claim 1 wherein said container further comprising a shelf extending into said interior area, said membrane supported by said shelf.

5. The writing implement sanitizer in accordance with claim 1 wherein said membrane is secured to said cover.

6. The writing implement sanitizer in accordance with claim 1 further comprising a pad located at said bottom end of said container and spaced from said membrane.

7. The writing implement sanitizer in accordance with claim 1 wherein said cover is releasably secured to said body.

8. The writing implement sanitizer in accordance with claim 1 wherein said sanitizer comprises a liquid sanitizer.

9. The writing implement sanitizer in accordance with claim 1 wherein said membrane is formed from a resilient material selected from the group consisting of: a sponge, foam, rubber and silicone.

10. The writing implement sanitizer in accordance with claim 1 wherein said bottom end of said container is closed whereby said container comprises a fluid containing area for fluid sanitizer below said membrane.

11. The writing implement sanitizer in accordance with claim 1 wherein said membrane has a top side and a bottom side and said bottom side is spaced from said bottom end of said body by a distance which permits a substantial portion of a writing implement to be located in said portion of said interior area below said membrane.

12. The writing implement sanitizer in accordance with claim 1 wherein said cover has at least two openings therein and said membrane has at least two passages there through, at least one of said passages aligned with each of said openings in said cover.

13. The writing implement sanitizer in accordance with claim 1 comprising a writing implement guide corresponding to each of said passages through said sanitization membrane.

* * * * *